United States Patent [19]

Niederer

[11] 4,199,824

[45] Apr. 29, 1980

[54] INTRAMEDULLARY STEM

[75] Inventor: Peter G. Niederer, Zollikofen, Switzerland

[73] Assignee: Sulzer Brothers Limited, Winterthur, Switzerland

[21] Appl. No.: 941,939

[22] Filed: Sep. 13, 1978

[30] Foreign Application Priority Data

Oct. 12, 1977 [CH] Switzerland ............... 12436/77

[51] Int. Cl.² ............................................. A61F 1/24
[52] U.S. Cl. .................................... 3/1.913; 3/1.91;
128/92 C; 128/92 CA
[58] Field of Search ................................ 3/1.9–1.913;
128/92 C, 92 CA

[56] References Cited

U.S. PATENT DOCUMENTS

| 3,067,740 | 12/1962 | Haboush | 128/92 CA |
| 3,510,883 | 5/1970 | Cathcart | 3/1.913 |
| 3,696,446 | 10/1972 | Bousquet et al. | 3/1.911 |
| 3,848,272 | 11/1974 | Noiles | 3/1.913 |
| 3,996,625 | 12/1976 | Noiles | 3/1.912 |
| 4,003,096 | 1/1977 | Frey | 3/1.91 |

*Primary Examiner*—Ronald L. Frinks
*Attorney, Agent, or Firm*—Kenyon & Kenyon

[57] ABSTRACT

The intramedullary stem is provided with a plurality of recesses in the wide sides which are disposed in herring bone fashion. These recesses communicate with a longitudinal groove so that bone tissue material may move into the recesses and grooves during implantation. Apertures may also be provided through the stem so as to provide spaces for the tissue material to collect in a packed manner. Each recess also has a domed shaped pocket on the upper side to receive the material during implantation.

10 Claims, 4 Drawing Figures

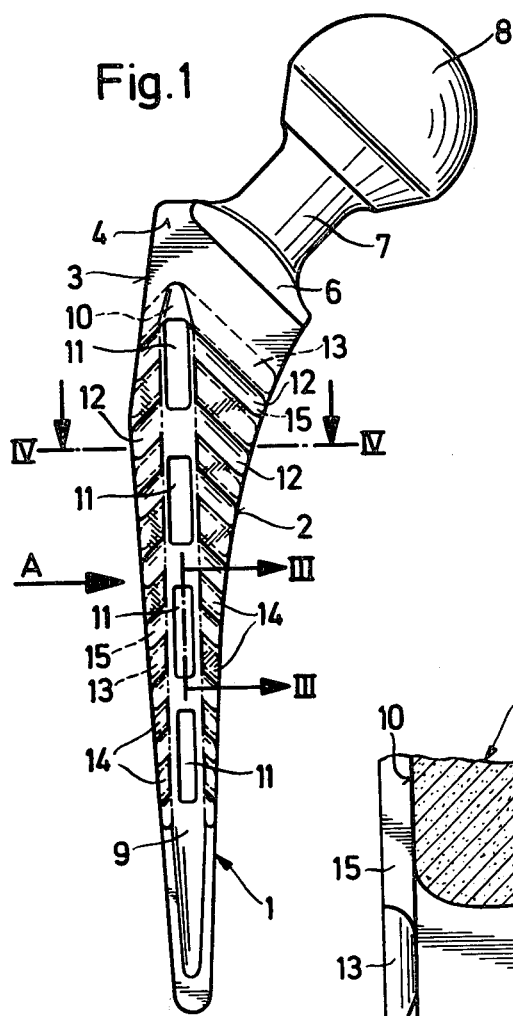
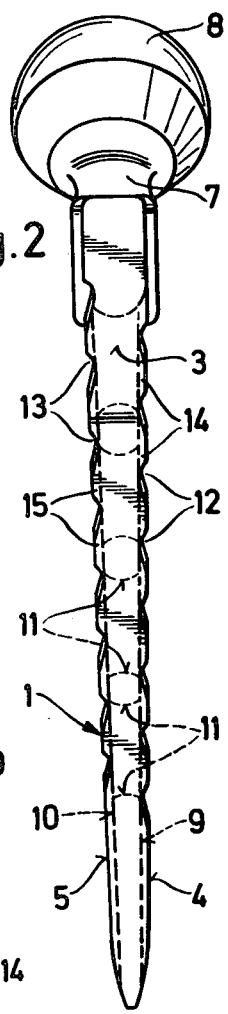
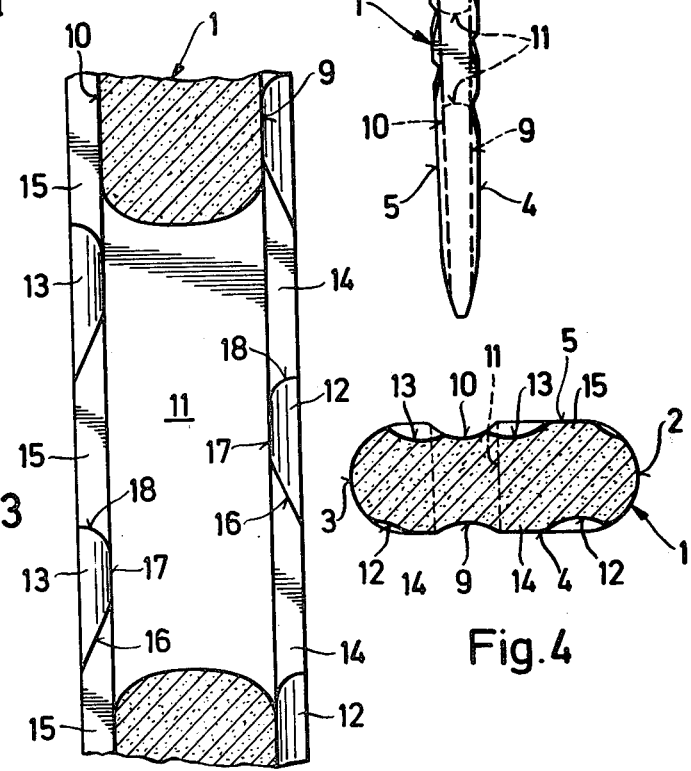
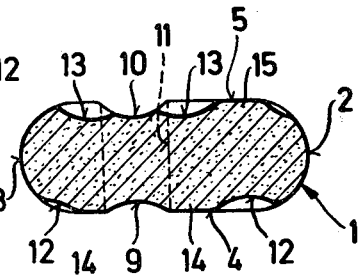

INTRAMEDULLARY STEM

This invention relates to an intramedullary stem for a bone implant, and more particularly to an intramedullary stem for a hip joint endoprosthesis.

Heretofore, in many bone implant procedures, it has been known to utilize an uncemented anchorage. In such cases, the intramedullary stem of the endoprosthesis is usually introduced into an operatively prepared recess in mainly spongy bone tissue. Usually, the internal dimensions of the recess are less than those of the stem. When the stem is being introduced, some of the spongy tissue is compressed and displaced and small fragments may occassionally crumble away. For rapid fiberous encapsulation of the stem both the "compressed" tissue and the "highly compacted" fragments should remain very uniformly distributed over the length of the stem in the receiving recess. However, this cannot be obtained in many instances.

Accordingly, it is an object of the invention to improve the distribution of displaced tissue and the anchorage of an intramedullary stem of an endoprosthesis implant.

It is another object of the invention to permit a rapid and strong fiberous encapsulation of an implanted stem of an endoprosthesis.

Briefly, the invention provides an intramdedullary stem for a bone implant which has a pair of at least approximately opposite sides, a longitudinally extending groove in each side and a plurality of recesses disposed in each side in herring bone pattern and terminating in the groove therein. These recesses are directed towards one end of the stem, that is, the end carrying a femoral head when the stem is part of a hip joint endoprosthesis.

Advantageously, the recesses form an angle of from 30° to 60° with the longitudinal axis of a respective groove.

The stem enables displaced tissue to "flow away" into the recesses where the tissue can be stored. If the longitudinal grooves are formed with longitudinally spaced apart apertures which communicate the grooves with each other, the material can collect from both sides via the recesses and grooves in the apertures. This material can then form webs of relatively densely packed tissue material which extends through the stem and improves anchorage. This densely packed material can rapidly consolidate for growing together.

Another advantage of the stem is that the deliberate "flow away" of the displaced tissue insures that the tissue which is thus displaced does not unnecessarily compress, and thus, damage tissue further away from the bone because of a lack of space to store the displaced tissue. Hence, destruction or damage of the tissue structure is reduced to very low levels.

In order to further improve the distribution of the displaced tissue, the recesses on one side are offset from the recesses on the other side. Also, if the unrecessed stem parts have rounded edges, little damage is done to the tissue during the introduction of the stem. Further, the "flow away" of the tissue material into the recesses and longitudinal grooves can be increased.

In order to further improve the "flowing and compacting" of the displaced tissue in the recesses, each recess may be formed with a cross-sectional shape including an upwardly inclined wall extending to a flat and vertical base and a curved wall extending from an upper end of the base to define a domed pocket.

These and other objects and advantages of the invention will become more apparent from the following detailed description taken in conjunction with the accompanying drawings wherein:

FIG. 1 illustrates side view of a hip joint prosthesis having an intramedullary stem according to the inventions;

FIG. 2 illustrates a view of the prosthesis looking in the direction indicated by the arrow A in FIG. 1;

FIG. 3 illustrates a view taken along line III—III of FIG. 1; and

FIG. 4 illustrates a view taken on line IV—IV of FIG. 1.

Referring to FIGS. 1 and 2, the hip joint endoprosthesis comprises an intramedullary stem 1 which has a straight longitudinal axis and is similar in shape to a blade, i.e. the dimensions of the stem 1 are such that two opposite sides 2, 3 are relatively narrow while the remaining sides 4, 5 are relatively wide. The cross-section is substantially in the shape of an elongated rectangle (see FIG. 4). However, the stem cross-section may be eliptical, polygonal, or at least substantially square, i.e. in the shape of a rectangle having sides substantially the same length as each other.

As shown, the proximal narrow side 2 of the stem is in the form of a curve whereas the distal narrow side 3 is in the form of two substantially straight surfaces which intersect each other at an angle at a discontinuity about three quarters of the way along the length of the stem 1 as viewed from the free end. The sides 2, 3 converge conically towards the free end so that the stem 1 narrows continuously downwardly as viewed. However, this is not essential for the purposes of the invention. The stem can therefore, if required, be bounded by parallel surfaces, i.e. the stem need not narrow. Alternatively, the stem may extend sinously along the longitudinal axis in the shape of a helical surface.

The stem terminates at the top end in a collar 6 which merges into a femoral neck 7 on which a femoral head 8 is disposed.

Each of the wide sides 4, 5 of the stem is formed with a longitudinal groove 9, 10 which extends downwardly, as viewed, at substantially the same depth. In addition, apertures 11 are spaced longitudinally along the stem 1 to communicate the grooves 9, 10 with each other.

Each side 4, 5 is also provided with a plurality of recesses 12, 13 which are disposed in a herring bone pattern. Each recess rises, as viewed, at an angle of approximately 45° and terminates in a groove 9, 10. The groove 9, 10 thus forms the "spine" of the herring bone pattern. The stem is provided with unrecessed parts 14, 15 between the recesses 12, 13. These parts 14, 15 can be rounded at the corners and edges to reduce damage to the spongy bone tissue when the stem 1 is being introduced and to facilitate the "flow" of displaced material. As indicated in FIG. 1, the recesses 12, 13 are offset relative to each other on the opposite sides 4, 5.

Referring to FIG. 3, each recess 12, 13 has a cross-sectional shape which includes an upwardly inclined wall or bottom boundary 16 which extends to a flat vertical base 17, the depth of which is at least substantially the same as the depth of a groove 9, 10, and a curved wall 18 which extends from the base 17 to define a domed pocket. The upwardly inclined wall 16 enables the displaced tissue material to enter the recess relatively easily. However, the upper curved wall 18 of the recess 12, 13 forms a dome in which at least some of the displaced material can collect and be compressed. When any of the recesses 12, 13 registers with any of the apertures 11, some of the material introduced into such recess 12, 13 is displaced from both sides into the aperture 11 and forms tissue webs which extend through the stem 1.

The endoprosthesis may be made of any suitable material. For example the materials used for the prosthesis and the stem can be made of metal, ceramics or plastics. Further, when made of metal, the prosthesis can be provided with a coating which can, if required, be osteogenetic.

What is claimed is:

1. An intramedullary stem for a bone implant having
   a pair of at least approximately opposite sides;
   a longitudinally extending groove in each said side; and
   a plurality of recesses disposed in each side in a herring bone pattern and terminating in said groove therein, said recesses being directed towards one end of said stem.

2. An intramedullary stem as set forth in claim 1 having a plurality of longitudinally spaced apertures, each aperture communicating said grooves with each other.

3. An intramedullary stem as set forth in claim 1 wherein said recesses on one of said sides are offset relative to said recesses of the other of said sides.

4. An intramedullary stem as set forth in claim 1 wherein each recess forms an angle of from 30° to 60° with the longitudinal axis of a respective groove.

5. An intramedullary stem as set forth in claim 1 which further has unrecessed parts between said recesses, each said unrecessed part having rounded edges.

6. An intramedullary stem as set forth in claim 1 wherein each recess has a cross-sectional shape including an upwardly inclined wall extending to a flat vertical base and a curved wall extending from an upper end of said base to define a domed pocket.

7. An intramedullary stem as set forth in claim 1 of sinuous shape along a longitudinal axis thereof.

8. A hip joint endoprosethesis comprising
   a stem having a pair of at least approximately opposite sides;
   a longitudinally extending groove in each said side; and
   a plurality of recesses disposed in each side in a herring bone pattern and terminating in said groove therein, said recesses being directed towards one end of said stem; and
   a femoral head at said one end.

9. A hip joint endoprothesis as set forth in claim 8 wherein said stem is of blade shape.

10. A hip joint endoprosthesis as set forth in claim 8 wherein said stem has a plurality of longitudinally spaced apertures, each aperture communicating said grooves with each other, and each said recess has a cross-sectional shape including an upwardly inclined wall extending to a flat vertical base and a curved wall extending from an upper end of said base to define a domed pocket.

* * * * *

UNITED STATES PATENT AND TRADEMARK OFFICE
CERTIFICATE OF CORRECTION

PATENT NO. : 4,199,824
DATED : April 29, 1980
INVENTOR(S) : Niederer, Peter G.

It is certified that error appears in the above—identified patent and that said Letters Patent is hereby corrected as shown below:

Column 1, line 28, change "intramdedullary" to

-- intramedullary --.

Column 4, line 24, change "endoprothesis" to

-- endoprosthesis --.

Signed and Sealed this

Thirtieth Day of September 1980

[SEAL]

Attest:

SIDNEY A. DIAMOND

Attesting Officer     Commissioner of Patents and Trademarks